United States Patent [19]

Smith

[11] 4,311,139

[45] Jan. 19, 1982

[54] METHOD AND APPARATUS FOR CATHETER INSERTION

[75] Inventor: Gordon E. Smith, Carrollton, Tex.

[73] Assignee: Quest Medical, Inc., Carrollton, Tex.

[21] Appl. No.: 134,933

[22] Filed: Mar. 28, 1980

[51] Int. Cl.³ .................... A61M 5/00; A61M 25/00
[52] U.S. Cl. ............................ 128/214.4; 128/349 R; 128/348; 128/214.2
[58] Field of Search .................. 128/214.4, 214.2, 347, 128/350 R, 348, DIG. 9, DIG. 16, 349 R

[56] References Cited

U.S. PATENT DOCUMENTS

| | | | |
|---|---|---|---|
| 3,000,380 | 9/1961 | Doherty | 128/214.4 |
| 3,010,453 | 11/1961 | Doherty | 128/214.4 |
| 3,017,884 | 1/1962 | Doherty et al. | 128/214.4 |
| 3,055,361 | 9/1962 | Ballard | 128/214.4 |
| 3,185,151 | 5/1965 | Czorny | 128/214.4 |
| 3,215,141 | 11/1965 | Podhora | 128/214.4 |
| 3,474,786 | 10/1969 | Spademan | 128/214.4 |
| 3,703,174 | 11/1972 | Smith | 128/214.4 |
| 3,714,945 | 2/1973 | Stanley | 128/214.4 |
| 3,826,256 | 7/1974 | Smith | 128/214.4 |
| 4,205,675 | 6/1980 | Vaillancourt | 128/214.4 |

Primary Examiner—Gene Mancene
Assistant Examiner—Michael J. Foycik
Attorney, Agent, or Firm—Isaksen, Lathrop, Esch, Hart & Clark

[57] ABSTRACT

A method and apparatus for catheter insertion (10 or 100) for inserting a flexible catheter (12 or 112) into a selected liquid-filled body cavity (144) into which the anterior end of a substantially rigid, tubular member (151) has been inserted. A containing member (22 or 122) adapted to contain a limp, flexible, substantially straight catheter (12 or 112) is attached to the posterior end of the tubular member (151) in fluid communication therewith. The apparatus (10 or 100) has means (34 or 137) for selectively applying positive and negative pressure to the chamber (22 or 122), first to withdraw liquid from the liquid-filled body cavity (144) through the tubular member (151) into the chamber (22 or 122) and, second, to expel the liquid back through the tubular member (151) and into the body cavity (144) to draw the catheter (12 or 112) by means of friction between the liquid and the body (14 or 114) of the flexible catheter (12 or 112) into the body cavity (144), with the body (14 or 114) of the catheter (12 or 112) extending through the tubular member (151) into the body cavity (144). The substantially rigid, tubular member (151) may then be withdrawn from the body cavity (144), leaving the anterior end of the flexible catheter (12 or 112) in place within the body cavity (144).

4 Claims, 8 Drawing Figures

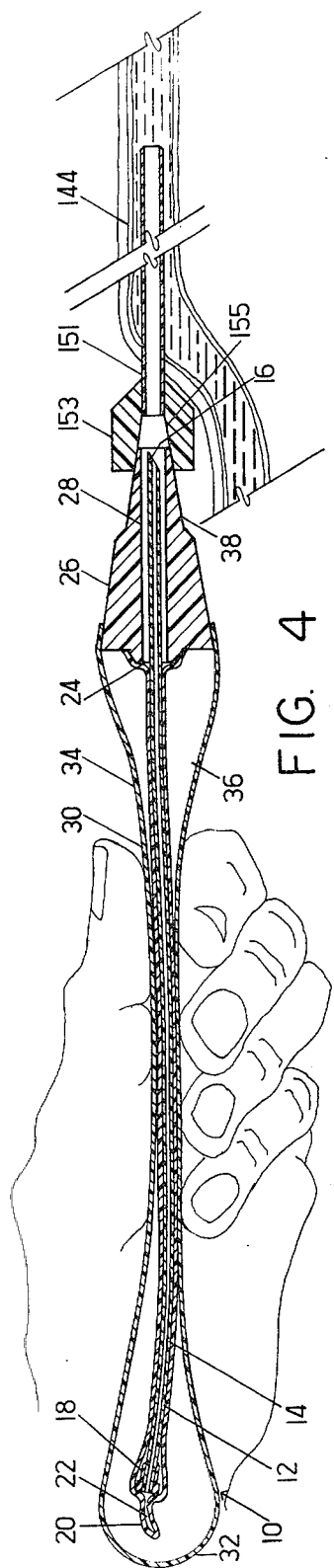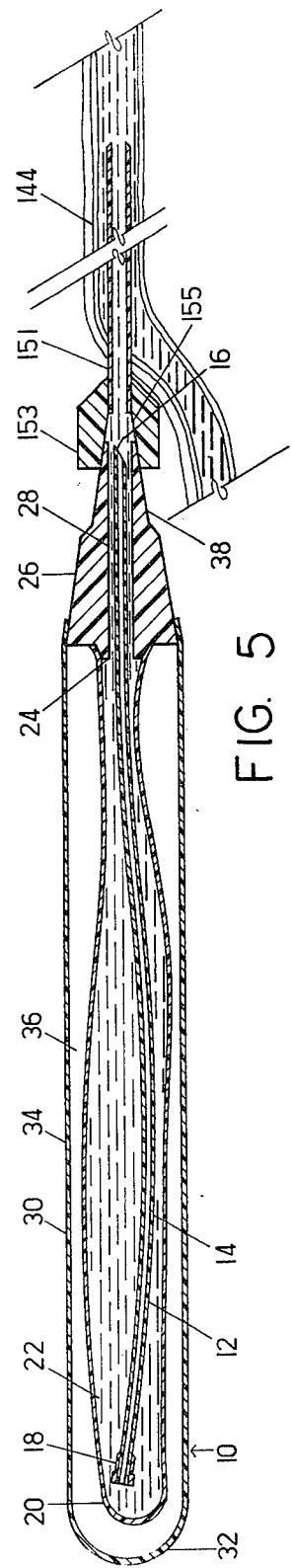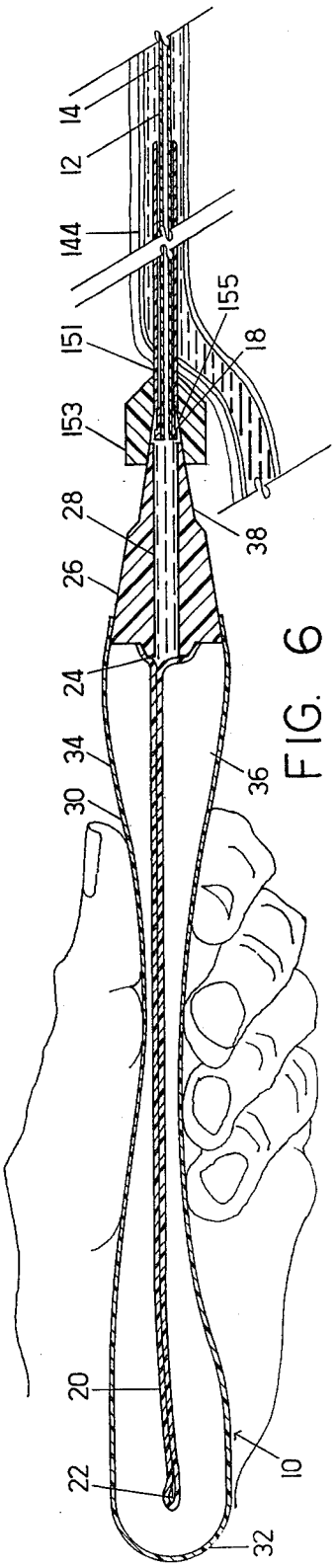

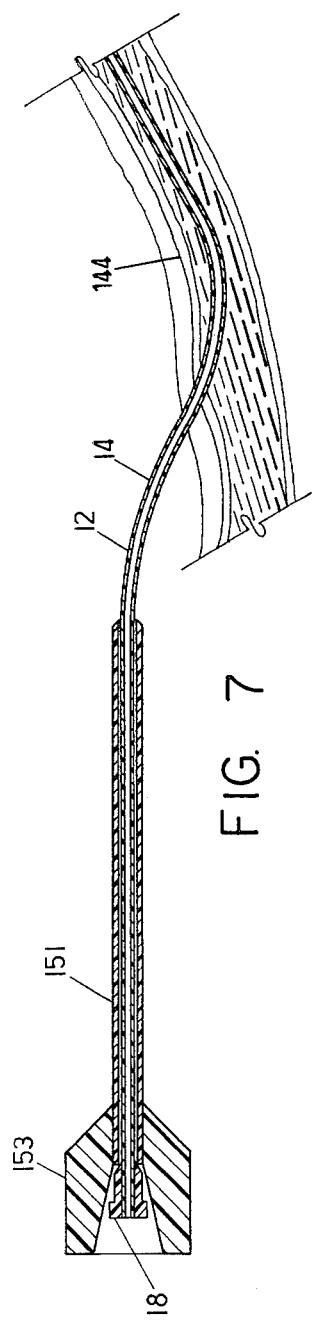
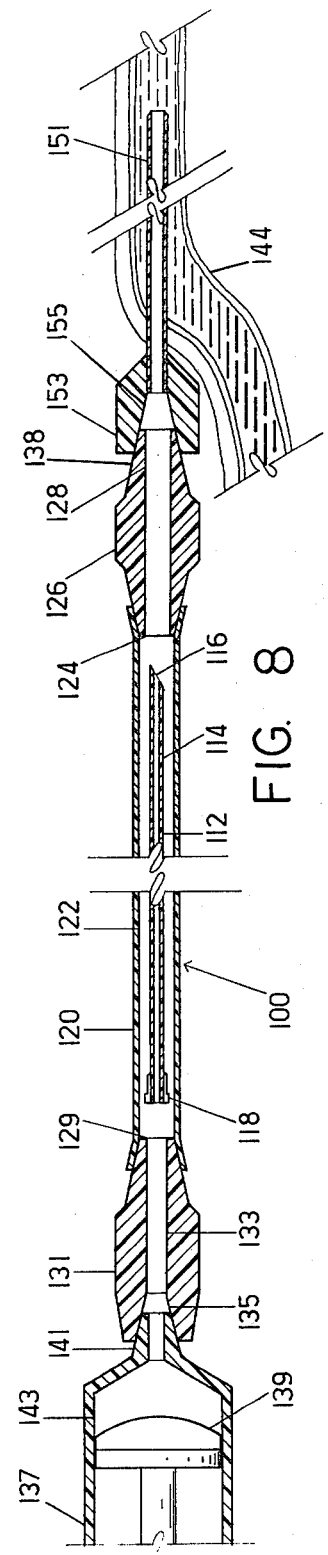

METHOD AND APPARATUS FOR CATHETER INSERTION

TECHNICAL FIELD

The present invention relates to catheters in general and, in particular, to a device for inserting a flexible catheter into the bloodstream of a patient.

BACKGROUND OF PRIOR ART

The prior art is generally cognizant of methods for inserting catheters of varying degrees of flexibility into blood vessels or other enclosed parts of the body. Stanley, U.S. Pat. No. 3,714,945, describes a device for inserting a semi-rigid catheter. In the Stanley device, a hollow needle or other rigid, piercing member is placed within a semi-rigid catheter prior to its insertion into the patient's body. The needle guides and supports the catheter while it creates the opening through which the catheter is passed. Once the needle with accompanying catheter has been properly placed in the blood vessel or other cavity, the needle is withdrawn, leaving the catheter behind and ready for use.

Smith, U.S. Pat. No. 3,826,256 and Smith, U.S. Pat. No. 3,703,174, show means for injecting a small, limp, and elastic catheter into a blood vessel or similarly enclosed part of the body. In both Smith devices a catheter having the characteristics described is wound in a small coil contained within the barrel of a syringe or similar fluid-tight holder that is filled with a suitable sterile fluid. The end of the catheter that is to be injected into the patient extends into the hollow interior of the needle of the syringe. Once the needle has been inserted into the blood vessel or other body cavity, the plunger of the syringe is depressed and a portion of the sterile fluid is injected into the patient through the needle. The friction between the fluid passing through the needle and the catheter contained therein is sufficient to flush the end of the cathether through the needle and into the blood vessel. As the end of the catheter is injected, it draws with it the trailing parts of the catheter, which uncoil and pass through the hollow needle. The trailing end of the catheter is provided with an enlargement of a size sufficient to prevent the entire catheter's being injected into the patient. The needle may be withdrawn from the patient, leaving the injected portions of the limp catheter in place.

For various reasons set forth in full in Smith, U.S. Pat. No. 3,703,174, a limp, flexible catheter is especially advantageous for use in situations in which a catheter must be left in place over an extended period of time. However, more rigid catheters of the sort described in Stanley may be adequate or even preferable when, for example, shortterm use is anticipated or a large diameter catheter is desired. Similarly, it may be desired to replace a large bore needle or a trocar already in place with a flexible and less trauma-producing catheter. For example, one way to determine the proper positioning of the end of a probing needle is to withdraw some of the fluid into which it extends to verify penetration to a particular cavity characterized by that fluid. The prior art, including the Smith patents referred to above, does not show a method or device for first withdrawing fluid through a needle and then, subsequently, inserting a limp and flexible catheter into the cavity penetrated by the needle with subsequent withdrawal of the needle in such a manner as to leave the catheter in place.

BRIEF SUMMARY OF THE INVENTION

The present invention is summarized in that a method for inserting a flexible catheter into a selected liquid-filled body cavity includes the steps of selecting a substantially rigid, tubular member having an anterior end and a posterior end and a selected minimum internal diameter and inserting the anterior end of the tubular member into the body cavity. A containing chamber is then engaged in fluid-tight relation to the posterior end of the tubular member in fluid communication therewith, the containing chamber containing a limp, flexible, substantially straight catheter having an anterior end and a posterior end and a retaining ring at the posterior end having a selected maximum diameter greater than the minimum internal diameter of the tubular member. Negative pressure is applied to the containing chamber, and the containing chamber is allowed substantially to fill with liquid drawn through the tubular member from the body cavity. Positive pressure is then applied to the containing chamber, expelling the liquid with which the containing chamber has been filled back into the body cavity through the tubular member, drawing the anterior end of the flexible catheter through the tubular member and into the body cavity and engaging the retaining ring with the posterior end of the tubular member. The containing chamber is then disengaged from the tubular member and the tubular member is withdrawn from the body cavity, leaving the anterior end of the flexible catheter in the body cavity.

An apparatus for inserting a flexible catheter into a selected liquid-filled body cavity into which the anterior end of a substantially rigid, tubular member has been inserted, the tubular member having an anterior and a posterior end and a selected minimum interior diameter, includes a limp, flexible, substantially straight catheter. The flexible catheter has a body having an anterior end and a posterior end and a retaining ring that surrounds the posterior end. The retaining ring has a selected maximum diameter greater than the minimum diameter of the substantially rigid, tubular member. A containing chamber is adapted to contain the flexible catheter and has means for attaching the containing chamber to the posterior end of the rigid, tubular member in removable fluid-tight relation and in fluid communication with the rigid, tubular member, the containing chamber having a flexible, fluid-tight wall. An elastically flexible, fluid-tight external casing is closed to the outside atmosphere and receives a selected quantity of fluid and the containing chamber therein so that the containing chamber can be exhausted by the application of an externally applied deforming force to the external casing and can be filled by the removal of the deforming force to allow the external casing to elastically return to its original shape.

A primary object of the invention is to provide for the insertion of a flexible catheter through a tubular body that is already inserted into the body cavity to be catheterized.

A second object of the invention is to provide an apparatus for inserting a flexible catheter in which the catheter is held substantially straight.

Another object of the invention is to provide a means for inserting a flexible catheter into a fluid-filled body cavity in which fluid from the body cavity is used to flush the anterior end of the flexible catheter into the body cavity.

A further object of the invention is to provide an apparatus for inserting a flexible catheter that is inexpensive to make and is simple and reliable in structure.

Other objects, features, and advantages of the invention will be apparent from the following detailed description taken in conjunction with the accompanying drawings showing preferred embodiments of apparatus for catheter insertion exemplifying the principles of the invention.

BRIEF DESCRIPTION OF THE DRAWINGS

FIG. 4 is a cross-sectional view taken along the longitudinal centerline of the apparatus shown in FIG. 1, with the external casing deformed upon compression by the hand of a user of the apparatus and the male needle fitting engaged in the female needle fitting of a semi-flexible catheter, the semi-flexible catheter extending into the vein of a patient.

FIG. 5 is a cross sectional view similar to FIG. 4, with the external casing having elastically regained its original shape after a deformation such as that shown in FIG. 4, the containing chamber being filled with blood drawn from the vein.

FIG. 6 is a cross sectional view similar to FIG. 4 with the external casing deformed upon recompression by the hand of the user of the apparatus after the filling of the containing chamber with blood as shown in FIG. 5, with the limp catheter drawn into the vein and engaged in the semi-flexible catheter.

FIG. 7 is a cross sectional view of the semi-flexible catheter and the limp catheter taken along the longitudinal centerline of the catheters, with the limp catheter extending into the vein of the patient with the semi-flexible catheter withdrawn from the vein.

FIG. 8 is a cross sectional view taken along the longitudinal centerline of a second embodiment of the apparatus for catheter insertion of the invention, with the male needle fitting engaged in the female needle fitting of a flexible catheter that extends into the vein of a patient.

DETAILED DESCRIPTION OF THE PREFERRED EMBODIMENT

Figure 1:
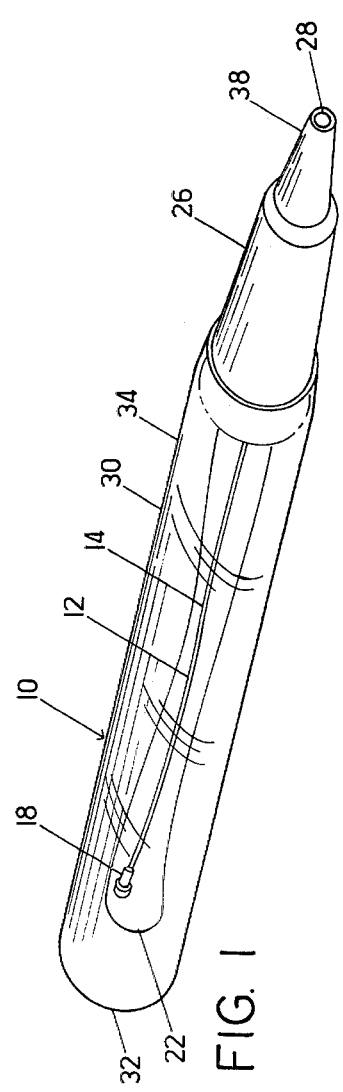
FIG. 1 is a side elevation view of an apparatus for catheter insertion constructed in accordance with the present invention.
Figure 2:
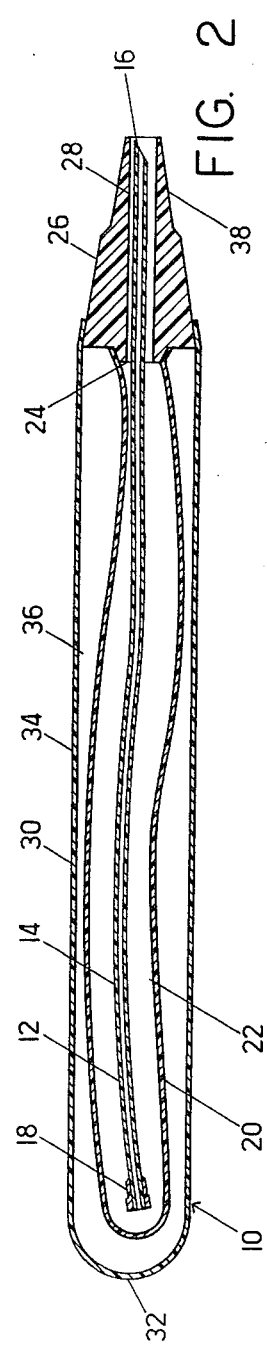
FIG. 2 is a cross sectional view taken along the longitudinal centerline of the apparatus of FIG. 1.
Figure 3:
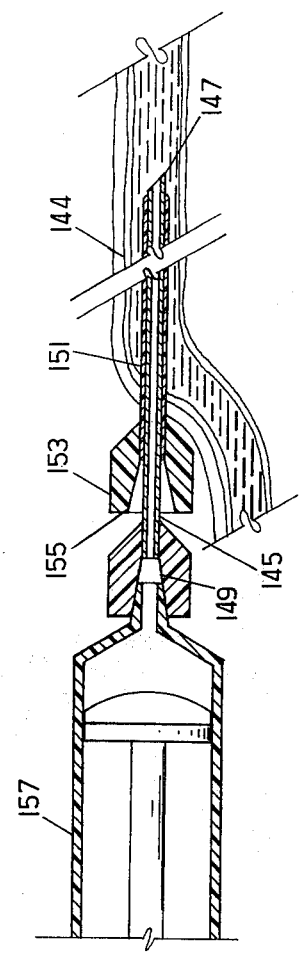
FIG. 3 is a cross sectional view of a conventional over the needle, semi-flexible catheter and associated needle and broken away portion of the associated syringe, taken along the longitudinal centerline thereof, after insertion of the catheter and needle into a vein of a patient.

Referring more particularly to the drawings, wherein like numbers refer to like parts, FIGS. 1, 2, 4, 5, and 6 show an apparatus for catheter insertion, generally indicated at 10, constructed in accordance with the present invention. The apparatus includes a catheter 12 having a tubular body 14 having a selected diameter and length, a beveled anterior tip 16, and a cylindrical retaining ring 18 surrounding and attached to the posterior end of the body 14 and having a selected maximum diameter greater than the diameter of the body 14. The catheter 12 is substantially straight and, with the retaining ring 18, is made of a flexible, limp, biologically inert material, such as silicone rubber.

The catheter 12 is substantially contained within a wall 20 having inwardly facing surfaces that define a substantially cylindrical, fluid-tight containing chamber 22. The chamber 22 may be filled with any selected fluid, air or normal saline being examples. The chamber 22 has an anteriorally facing, substantially circular mouth 24. The mouth 24 is attached to a headpiece 26 in fluid-tight relation. The headpiece has internal surfaces defining a substantially cylindrical headpiece passage 28 that is substantially continuous with the mouth 24 and extends through the headpiece to open anteriorally, thus communicating with the atmosphere surrounding the apparatus. Both the mouth 24 and the passage 28 have minimum diameters selected to be larger than the maximum diameter of the retaining ring 18, allowing the ring 18 to readily pass therethrough. The anterior end of the catheter 12 extends from the chamber 22 into the headpiece passage 28 for a selected distance. Preferably, the wall 20 of the chamber 22 is made of a limp, flexible, fluid-tight, and water resistant material such as thin polypropylene sheet material.

A substantially tubular wall 30 having a closed end 32 forms an external casing 34 that loosely encloses the wall 20 and is attached to the headpiece 26 in fluid-tight relation, so that a completely enclosed fluid-tight space 36 is formed between inner surfaces of the external casing 34 and outer surfaces of the wall 20. The external casing 34 is made of an elastically flexible material, the flexibility of which is selected to be such that a user of the apparatus may readily deform the external casing 34 by compressing it between his thumb and fingers. When the external casing 34 is so deformed, the volume of the space enclosed therein is reduced, thereby increasing the pressure of the fluid enclosed in the fluid-tight space 36. Consequently, the wall 20 is subjected to increased external pressure and collapses, exerting a positive pressure on the fluid contained therein, whereby the fluid is exhausted from the apparatus through the mouth 24 and contiguous headpiece passage 28. When the user releases the pressure exerted by his thumb and fingers against the external casing 34, the external casing elastically returns to its original shape, releasing the pressure on the fluid enclosed within the fluid-tight space 36, so that a negative pressure in relation to the atmosphere surrounding the apparatus is created within the chamber 22. By this means, a user of the apparatus first may force out the fluid contained within the chamber 22 and then cause the chamber to become filled with any fluid that is allowed to enter the headpiece passage 28. The procedure of first compressing the external casing 34 shall be referred to hereinafter as "exhausting" the fluid contained in chamber 22. Releasing the external casing 34 and thereby causing any fluid entering the passage 28 to fill the chamber 22 shall be referred to hereinafter as the "filling" procedure.

The anterior end of the headpiece 26 has surfaces defining a male needle fitting 38 disposed in coaxial relation with the headpiece passage 28. Preferably, the male needle fitting 38 is substantially conical and adapted to mateably engage conventional female needle fittings in fluid-tight, mating relation.

FIG. 8 shows a second embodiment of the invention, shown generally at 100. The apparatus has a catheter 112 generally equivalent to the catheter 12 described above. The catheter 112 has a tubular body 114 with a selected diameter and length, a beveled anterior tip 116, and a cylindrical retaining ring 118 surrounding and attached to the posterior end of the body 114 and having a selected maximum diameter larger than the diameter of the body 114. A substantially tubular wall 120 has interior surfaces defining a chamber 122 having a diameter and length selected to be large enough to contain the catheter 112 in a substantially straight position coaxial with the tubular wall 120. The chamber 122 is filled with a selected fluid such as air or normal saline.

The chamber 122 has an anteriorally facing, substantially circular mouth 124. A headpiece 126 engages the mouth 124 in fluid-tight relation. A substantially cylindrical headpiece passage 128 is coaxial with the tubular wall 120 and is substantially a continuation of the mouth 124. The headpiece passage 128 extends through the headpiece 126, opening anteriorally. The passage 128 and mouth 124 have minimum diameters larger than the maximum diameter of the retaining ring 118, allowing the ring to readily pass therethrough. The anterior end of the headpiece 126 has surfaces defining a male needle fitting 138 coaxial with the passage 128. Preferably, the male needle fitting 138 is substantially conical and adapted to mateably engage conventional female needle fittings in fluid-tight, mating relation.

The chamber 122 has a posteriorally facing mouth 129. A tailpiece 131 has internal surfaces defining a tailpiece passage 133 extending from front to back entirely through the tailpiece. The tailpiece 131 is attached to the posteriorally facing mouth 129 in fluid-tight relation and in such an orientation that the anterior end of the tailpiece passage 133 communicates with the chamber 122.

Surfaces within the tailpiece passage 133 define a rearwardly facing female needle fitting 135 adapted to engage a male needle fitting in fluid-tight relation. Preferably, the female needle fitting 135 is a conical taper of the proportions conventionally used in standard syringes and needles used in conventional medical care. A means for selectively applying positive and negative pressures to the interior of the chamber 122 is attached to the female needle fitting 135 in fluid-tight relation. Preferably, a conventional syringe 137 is used, the syringe having a barrel 143, a piston 139, and a conventional male needle fitting 141 adapted to engage the female needle fitting 135 in fluid-tight relation.

With the male needle fitting 141 of the syringe engaged in the female needle fitting 135, the piston 139 is depressed to its fullest degree, expelling the fluid contained within the barrel 143 and reducing to a minimum the combined volumes of the barrel 143, the passages 133 and 128, and the chamber 122. Alternatively, the syringe 137 may be attached to the needle fitting 135 with its piston 139 already depressed. In either event, the process whereby the means for selectively applying positive and negative pressures is attached to the female needle fitting 135 and is put in a condition whereby a negative pressure subsequently may be exerted therewith on the contents of the chamber 122 shall be referred to hereinafter as "exhausting" the fluid contained in chamber 122.

With the apparatus 100 exhausted, a user then withdraws the piston 139 to a desired extent, thereby exerting a negative pressure on the fluid within the chamber 122 relative to the surrounding atmosphere. By this means, a user of the apparatus 100 may cause the chamber 122 to become filled with any fluid that is allowed to enter the headpiece passage 128 while the piston 139 is being withdrawn. If it is desired, the fluid that is filling the chamber 122 may be allowed also to enter and partially fill the barrel 143. The procedure of applying a negative pressure relative to the surrounding atmosphere to the contents of the chamber 122 and thereby causing any fluid allowed to enter the headpiece passage 128 to fill the chamber 122 shall be referred to hereinafter as the "filling" procedure.

The method of the invention is described as follows. First, the anterior end of a substantially rigid, tubular member is introduced into the body cavity into which the user desires to insert a flexible catheter, hereinafter assumed to be a vein 144. The substantially rigid, tubular member may be a conventional hollow needle or trocar. Alternatively, the substantially rigid, tubular member may be a semi-flexible catheter of a conventional sort. For the purposes of illustration, the insertion of a semi-flexible catheter will be described.

A conventional hollow needle 145 having a selected diameter and an anterior, beveled point 147 is attached to a female needle fitting 149 in a conventional manner. A conventional, semi-flexible, tubular catheter 151 having an interior diameter less than the maximum diameter of the retaining ring 18 or 118 and equal to or slightly greater than the diameter of the needle 145 extends in a sleeve-like manner for substantially the length of the needle. A hub member 153 surrounds and is attached to the posterior end of the catheter 151 and has interior surfaces defining a conventional, rearwardly facing, female needle fitting 155. The needle 145 may be attached by means of its needle fitting 149 to a conventional syringe in order to provide a handle to allow the easier manipulation of the needle 145 or to withdraw liquid through the needle as a means of identifying the position of the anterior end of the needle. The needle 145 and associated semi-flexible catheter 151 are inserted into the vein 144. The needle 145 is withdrawn from the semi-flexible catheter 151, leaving the anterior end of the semi-flexible catheter inserted within the vein 144.

An apparatus 10 or 100 is exhausted, and the male needle fitting 38 or 138 is inserted into the female needle fitting 155 of the semi-flexible catheter 151, engaging it in substantially fluid-tight relation. The filling procedure for the apparatus 10 or 100 is then performed, causing the blood within the vein 144 to be drawn through the semi-flexible catheter 151 and the headpiece passage 28 or 128 and into the chamber 22 or 122, substantially filling the chamber 22 or 122. Next, the blood contained in the chamber 22 or 122 is forced back through the semi-flexible catheter 151 into the vein 144 by compressing the external casing 34 in the embodiment shown at 10 or by applying a positive pressure to the contents of chamber 122, preferably by depressing the piston 139 of the syringe 137, in the embodiment shown at 100. The forcing of the liquid contained in the chamber 22 or 122 into the body cavity involved hereinafter shall be referred to as "expelling" the liquid.

The friction between the blood being expelled through the headpiece passage 28 or 128 and the surface of the tubular body 14 or 114 of the catheter 12 or 112 draws the catheter through the headpiece passage and on through the semi-flexible catheter 151 until the retaining ring 18 or 118 comes to rest in and is held in fluid-tight relation by the female needle fitting 155 of the semi-flexible catheter 151. The anterior end of the catheter 12 or 112 is thereby expelled through the semi-flexible catheter into the vein 144. The beveled tip 16 or 116 of the catheter 12 or 112 aids in guiding the catheter through the needle fitting 155 and semi-flexible catheter 151.

The apparatus 10 or 100 is then disengaged from the needle fitting 155 of the semi-flexible catheter 151. The semi-flexible catheter 151 is then withdrawn from the body of the patient, leaving the anterior end of the catheter 12 or 112 within the vein 144. The semi-flexible catheter 151 may then be taped or otherwise fastened to the body of the patient, and fluids may be introduced through or withdrawn from the catheter 12 or 112 by attaching the appropriate tube or instrument to the needle fitting 155. Alternatively, the catheter 12 or 112 may be grasped at the point at which it emerges from the anterior end of the semi-flexible catheter 151 and firmly held while the semi-flexible catheter is gently drawn over the retaining ring 18 or 118. Thereafter appropriately formed fittings may be attached directly to the catheter 12 or 112.

As an alternative to the initial exhaustion procedure referred to above, the chamber 22 or 122 may be filled with an appropriate fluid such as sterile saline prior to the attachment of the device 10 or 100 to the needle fitting 155 of the semi-flexible catheter. The saline or other fluid may then be expelled into the vein 144, drawing the catheter 12 or 112 through the semi-flexible catheter 151, as described above.

It is understood that the present invention is not limited to the particular construction and arrangement of parts illustrated and disclosed nor to the particular steps disclosed herein. Instead, it embraces all such modified forms thereof as come within the scope of the following claims.

I claim:

1. A method for inserting a flexible catheter (12) into a selected liquid-filled body cavity (144) comprising the steps of
    (a) inserting the anterior end of a rigid, tubular member having a selected minimum internal diameter into the body cavity (144),
    (b) deforming the external casing (34) of a containing chamber (22) having a wall (20) made of flexible, fluid-tight material having an outer surface and being enclosed within an elastically flexible external casing (34) having an inner surface, and having a completely enclosed fluid-filled space (36) defined by the inner surface of the external casing (34) and the outer surface of the wall (20), the containing chamber (22) containing a limp, flexible, substantially straight catheter (12) having an anterior end and a posterior end and a retaining ring (18) at the posterior end having a selected maximum diameter greater than the minimum internal diameter of the tubular member, the deformation decreasing the volume of the fluid-filled space (36), increasing the pressure of the fluid enclosed in the fluid-filled space (36), and subjecting the wall (20) to increased pressure substantially to exhaust the containing chamber (22),
    (c) engaging the containing chamber (22) in fluid tight relation to the posterior end of the tubular member in fluid communication therewith,
    (d) allowing the external casing (34) to elastically return to its original shape to relieve the pressure on the fluid enclosed within the fluid-filled space (36) and apply a negative pressure to the containing chamber (22), thus substantially filling the containing chamber (22) with liquid drawn through the tubular member from the body cavity (144),
    (e) deforming the external casing (34) to decrease the volume of the fluid-filled space (36) to increase the pressure of the air enclosed in the fluid-filled space (36) and apply positive pressure to the containing chamber (22), thus expelling the liquid with which the containing chamber (22) has been filled back into the body cavity (144) through the tubular member, drawing the anterior end of the flexible catheter (12) through the tubular member and into the body cavity (144) and engaging the retaining ring (18) with the posterior end of the tubular member, and
    (f) disengaging the containing chamber (22) from the tubular member and withdrawing the tubular member from the body cavity (144), leaving the anterior end of the catheter (12) in the body cavity (144).

2. An apparatus (10) for inserting a flexible catheter (12) into a selected liquid-filled body cavity (144) into which the anterior end of a substantially rigid, tubular member (151) has been inserted, the tubular member (151) having an anterior and a posterior end and a selected minimum interior diameter, comprising:
    (a) a limp, flexible, substantially straight catheter (12) having a body (14) having an anterior end and a posterior end and a retaining ring (18) at the posterior end, the retaining ring (18) having a selected maximum diameter greater than the minimum diameter of the tubular member (151),
    (b) a containing chamber (22) adapted to contain the catheter (12) in a substantially straight position and, the containing chamber (22) having a flexible, fluid-tight wall (20), and
    (c) the chamber having an anteriorly facing mouth (24),
    (d) a headpiece (26) attached to the mouth (24) in fluid-tight relation, the headpiece (26) having internal surfaces defining a substantially cylindrical headpiece passage (28) that is substantially continuous with the mouth (24) and extends through the headpiece (26) to open anteriorly, and with the anterior end of the catheter (12) extending from the chamber (22) into the headpiece passage (28) for a selected distance, and
    (e) an elastically flexible, fluid-tight external casing (34) closed to the outside atmosphere and receiving a selected quantity of fluid and the containing chamber (22) therein so that the containing chamber (22) can be exhausted by the application of an externally applied deforming force to the external casing (34) and can be filled by the removal of the deforming force to allow the external casing (34) to elastically return to its original shape.

3. The apparatus for catheter insertion (10) of claim 2 in which the wall (20) is made of a limp, flexible, plastic sheet material.

4. The apparatus for catheter insertion (10) of claim 2 in which the external casing (34) includes a substantially tubular wall (30) having a closed end (32) and is attached to the headpiece (26) in fluid-tight relation.

* * * * *